United States Patent [19]

Chenard

[11] Patent Number: 4,611,001
[45] Date of Patent: Sep. 9, 1986

[54] ANTIMYCOTIC PYRAZOLOTETRATHIEPINS

[75] Inventor: Bertrand L. Chenard, Wilmington, Del.

[73] Assignee: E. I. Du Pont de Nemours and Company, Wilmington, Del.

[21] Appl. No.: 731,730

[22] Filed: May 8, 1985

[51] Int. Cl.$^4$ .................... A61K 31/55; C07D 495/04
[52] U.S. Cl. .................... 514/407; 548/370
[58] Field of Search .................. 548/370; 514/407

[56] References Cited

U.S. PATENT DOCUMENTS

| 4,275,073 | 6/1981 | Moberg | 548/370 |
| 4,515,801 | 5/1985 | Stegelmeier et al. | 548/370 |
| 4,529,735 | 7/1985 | Kuhle et al. | 548/370 |

OTHER PUBLICATIONS

Thornber, Chem. Soc. Rev., 8, pp. 563–580 (1979).
Gordon et al., The Chemist's Companion, pp. 107–109 (1972).
Burger's Medicinal Chemistry, 4th Edit., pp. 397–404, (1980).
Structural Effects on Equilibria in Organic Chem., Hine, pp. 110–117 (1975).
Remington's Pharmaceutical Sciences, 14th Edit., 1970, pp. 527–532.
Feher, F., Engelen, B., in Z. Naturforsch. B, 34B, 426–430 (1979).
Feher, F., Malcharek, F., Glinka, K., in Angew. Chem. Int. Ed., 10, 331 (1971).
Giolando and Rauchfuss in Organometallics, 3, 487–9 (1984).
Chenard and Miller, J. Org. Chem., 49, 1221–1224 (1984).

Primary Examiner—Richard A. Schwartz
Assistant Examiner—Kurt G. Briscoe

[57] ABSTRACT

Pyrazolotetrathiepins such as (a) 2,2-dimethyl-7-methyl-1,3,4,5-pyrazolotetrathiepin, (b) 2,2-dimethyl-7-phenyl-1,3,4,5-pyrazolotetrathiepin, (c) 4,4-dimethyl-7-methyl-1,2,3,5-pyrazolotetrathiepin, (d) 4,4-dimethyl-7-phenyl-1,2,3,5-pyrazolotetrathiepin, and (e) 3,3-dimethyl-7-methyl-1,2,4,5-pyrazolotetrathiepin are antimycotic agents.

30 Claims, No Drawings

ANTIMYCOTIC PYRAZOLOTETRATHIEPINS

BACKGROUND OF THE INVENTION

1. Field of the Invention

This invention relates to pyrazolotetrathiepins, processes for their preparation, pharmaceutical compositions containing them, and their use as antimycotic agents.

2. Prior Art

The pyrazolotetrathiepins of this invention are novel. The only known fused tetrathiepins are benzotetrathiepins. Representative of the state of the art relative to benzotetrathiepins are the following two publications:

Feher, F., Engelen, B. in *Z. Naturforsch.* B, 34B, 426–430 (1979) describe the X-ray structure analysis of 1,2,4,5-benzotetrathiepin and 3-methyl-1,2,4,5-benzotetrathiepin. No utility for these compounds was described.

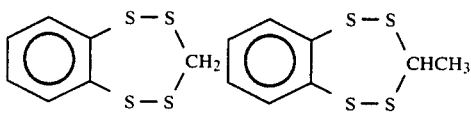

Feher, F., Malcharek, F., Glinka, K. in *Angew. Chem. Int. Ed.*, 10 331 (1971) disclose the preparation of several 1,2,4,5-benzotetrathiepins by the following reaction:

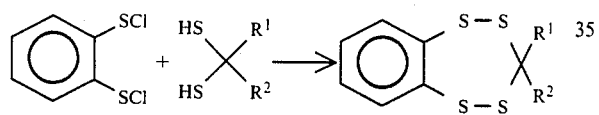

wherein $R^1$=H, methyl; $R^2$=H, methyl. No utility was described. This procedure will not produce 1,3,4,5-and 1,2,3,5-tetrathiepins.

Giolando and Rauchfuss in *Organometallics*, 3, 487–9 (1984) describe the reaction of aqueous ammonium sulfide with an organometallic polysulfide and acetone to form a six membered ring with a transition metal. The process of the present invention affords only seven-membered rings.

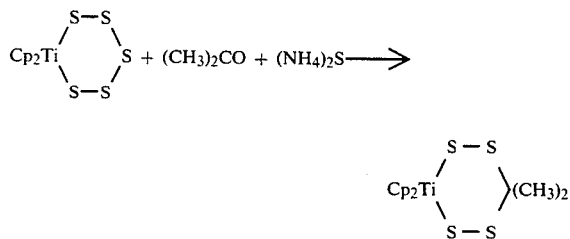

A variety of heterocyclic fused pentathiepins, and in particular certain pyrazolopentathiepins are known. For instance, 8-substituted pyrazolopentathiepins and related compounds are disclosed in coassigned pending U.S. application Ser. No. 543,195, filed on Oct. 18, 1983, in the name of B. L. Chenard. These compounds have the formula:

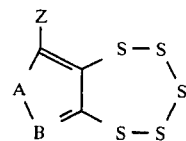

wherein amongst others A is $R^1N$ and B is N or $CR^2$. The preferred pyrazolopentathiepins are effective in fungicidal and photosensitizer compositions.

U.S. Pat. No. 4,275,073 issued June 23, 1981 to W. K. Moberg describes 7-substituted pyrazolopentathiepins of the formula:

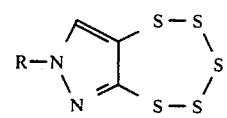

where R can be H, $C_1$–$C_6$ alkyl, $C_5$–$C_6$ cycloalkyl, benzyl and phenyl amongst others. These compounds are described to be useful as agricultural fungicides.

SUMMARY OF THE INVENTION

According to the present invention compounds are provided having the formula:

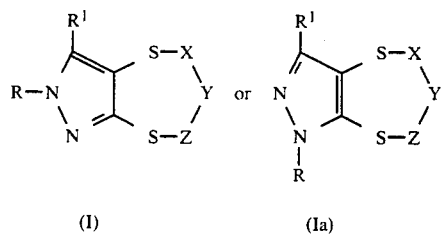

wherein

R is alkyl of 1–6 carbon atoms, cycloalkyl of 5–6 carbon atoms, benzyl, or phenyl which may be substituted with up to two groups selected from F, Cl, Br, $NO_2$, or $OCH_3$;

$R^1$ is hydrogen, halogen, or alkyl or 1–6 carbon atoms; and

X, Y, and Z are independently selected from S and $CR^2R^3$ where $R^2$ and $R^3$ individually are alkyl or 1–4 carbon atoms or together are alkylene of 3–6 carbon atoms, provided that:

(1) one of X, Y, and Z must be $CR^2R^3$ and two of X, Y, and Z are S; and (2) when R is phenyl; Y must be S.

Also provided are pharmaceutical compositions comprising a suitable pharmaceutical carrier and a compound of Formula (I) or (Ia), and methods of using the compounds of Formula (I) and (Ia) as antimycotics.

Also provided are processes for the preparation of the tetrathiepins of formula (I) and (Ia) by reacting a corresponding pentathiepin with a ketone, $R^2R^3CO$, wherein $R^2$ and $R^3$ have the values discussed above, and aqueous ammonium sulfide.

PREFERRED EMBODIMENTS

Preferred tetrathiepins are those of formula (I) or (Ia) wherein:

(1) R is phenyl or $CH_3$; or (2) $R^1$ is hydrogen.

More preferred are the tetrathiepins wherein $R^2$ and $R^3$ individually are methyl or taken together are pentamethylene.

Specifically preferred compounds because of their biological activity and ease of synthesis are:
(a) 2,2-Dimethyl-7-methyl-1,3,4,5-pyrazolotetrathiepin.
(b) 2,2-Dimethyl-7-phenyl-1,3,4,5-pyrazolotetrathiepin.
(c) 4,4-Dimethyl-7-methyl-1,2,3,5-pyrazolotetrathiepin.
(d) 4,4-Dimethyl-7-phenyl-1,2,3,5-pyrazolotetrathiepin.
(e) 3,3-Dimethyl-7-methyl-1,2,4,5-pyrazolotetrathiepin.

DETAILED DESCRIPTION OF THE INVENTION

Synthesis

The compounds of formula (I) and (Ia) can be prepared as shown below by adding aqueous ammonium sulfide to a mixture of a requisite pentathiepin and a ketone, of the formula $R^2R^3CO$, and carrying out the reaction until completion.

Generally the reaction time is a few minutes to several hours, and the reaction temperature can range from $-20°$ to $100°$ C. Preferably the reaction is run at room temperature.

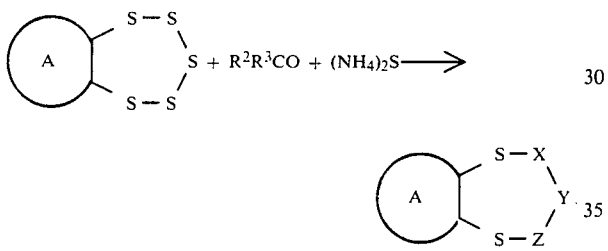

wherein

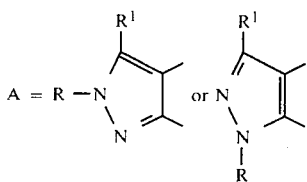

The process is conveniently carried out at atmospheric pressure, but it can also be carried out at pressures above or below atmospheric. It is not necessary that the process be carried out in an inert atmosphere since atmospheric oxygen is not harmful to the process.

The ratio of ammonium sulfide to pentathiepin employed in the process is not critical, but it is preferred to employ excess ammonium sulfide, e.g., a ratio of about 2:1 to 5:1. Although a minimum ratio of ketone to pentathiepin of about 1:1 is preferred, the ketone is frequently employed in excess and serves as a solvent.

When the starting pentathiepin is poorly soluble in the ketone reactant, it is preferred to employ an inert solvent. While suitable solvents include chlorinated solvents such as dichloromethane, dichloroethane, and chlorobenzene, other inert solvents can be used.

The tetrathiepin reaction product is isolated by standard methods. It can be purified by chromatography on silica gel, HPLC, crystallization, or by other known separation methods.

The following are illustrative examples of the invention in which all parts and percentages are by weight, and all degrees are Celsius unless otherwise noted.

PREPARATION OF EXAMPLES 1-3

(1) A mixture of 2,2-Dimethyl-7-phenyl-1,3,4,5-pyrazolotetrathiepin [$Y=Z=S$; $X=C(CH_3)_2$] and 4,4-Dimethyl-7-phenyl-1,2,3,5-pyrazolotetrathiepin [$X=Y=S$; $Z=C(CH_3)_2$]

(2) 2,2-Dimethyl-7-phenyl-1,3,4,5-pyrazolotetrathiepin [$Y=Z=S$; $X=C(CH_3)_2$]

(3) 4,4-Dimethyl-7-phenyl-1,2,3,5-pyrazolotetrathiepin [$X=Y=S$; $Z=C(CH_3)_2$]

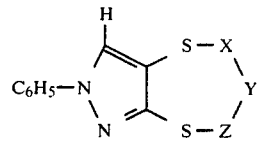

7-Phenylpyrazolopentathiepin, mp 113°-115°, is described in Table 3 of U.S. Pat. No. 4,275,073 and can be prepared using the general procedures of Examples 3 and 5 of that patent.

To a slurry of 7-phenylpyrazolopentathiepin (1.08 g, 3.57 mmol) in acetone (40 mL) was added 23% aqueous ammonium sulfide (2.6 mL, 8.8 mmol) over 30 min. Methylene chloride (10 mL) was added and the mixture was stirred 2 h. The solvent was removed at reduced pressure and the residue was diluted with water and extracted with methylene chloride (3×). The organic layers were combined, washed with brine, and dried through a cone of calcium sulfate. The light brown oil obtained on concentration was flash chromatographed on silica gel (column size: 5.1×20.3 cm, 5% ether/hexane eluent, 100 mL fractions) to give: 200 mL, nil; 100 mL, sulfur (unweighed); 400 mL, nil; 300 mL, 170 mg oily solid; 100 mL, 70 mg oil; 300 mL, 290 mg oil; 100 mL, 100 mg oil; 1000 mL, 190 mg oil. NMR of these fractions showed that all contained mixtures of isomers of the product. These fractions were further purified by HPLC (silica gel, 50% or 75% methylene chloride/hexane) to give in order of elution: recovered starting pentathiepin, 30 mg; 3,3-dimethyl-7-phenyl-1,2,4,5-pyrazolotetrathiepin, 150 mg; nmr (80 MHz)δ 8.1(s, 1H), 7.75-7.25(m, 5H), 2.2(s, 3H), 1.7(s, 3H); ir(KBr) 1596,1505,753; mp 88°-90°; m/e 311.9893, m/e calcd for $C_{12}H_{12}N_2S_4$: 311.9884; a mixture of 2,2-dimethyl-7-phenyl-1,3,4,5-pyrazolotetrathiepin and 4,4-dimethyl-7-phenyl-1,2,3,5-pyrazolotetrathiepin, (Example 1) 140 mg, m/e 311.9856.

In a similar experiment, in which 10 mL of methylene chloride was added to the reaction mixture before addition of the ammonium sulfide solution, the three isomeric tetrathiepins obtained were effectively separated by HPLC and were further characterized as follows:

3,3-dimethyl-7-phenyl-1,2,4,5-pyrazolotetrathiepin: inactive by-product: mp 92°-93° (ether/hexane); ir(KBr) 3140(m), 1592(m), 1511, 1340(m), 1048(m), 949(m), 853, 700(m), 680(m); yield, 250 mg (22%);

2,2-dimethyl-7-phenyl-1,3,4,5-pyrazolotetrathiepin: (Example 2): mp 140.5°-143.5° (ether/hexane); ir(KBr) 3142(m), 1599(m), 1508, 1050(m), 951, 756, 701(m), 685; nmr(80 MHz)δ 8.1(s, 1H), 7.9-7.3(m, 5H), 1.75(broadened s, 6H); m/e 311.9880; yield 240 mg (21%);

4,4-dimethyl-7-phenyl-1,2,3,5-pyrazolotetrathiepin: (Example 3): mp 134.5°-135.5° (ether/hexane); ir(KBr)

3130(m), 1595(m), 1508, 1331(m), 1195(m), 1100(m), 1050(m), 949, 810(m), 760, 700(m), 688(m); nmr(80 MHz)δ 8.1(s, 1H), 7.9–7.3(m, 5H), 1.8 (broadened s, 6H); m/e 311.9886; yield 160 mg (14%).

To further define the structure of the isomers, the structure of 2,2-dimethyl-7-phenyl-1,3,4,5-pyrazolotetrathiepin (Example 2) was confirmed by x-ray analysis.

PREPARATION OF EXAMPLES 4 AND 5

(4) 3,3-Dimethyl-7-methyl-1,2,4,5-pyrazolotetrathiepin [X=S,Y=C(CH$_3$)$_2$]
(5) 2,2-Dimethyl-7-methyl-1,3,4,5-pyrazolotetrathiepin [Y=S,X=C(CH$_3$)$_2$]

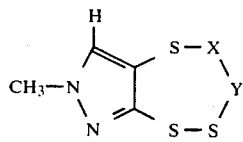

7-Methylpyrazolopentathiepin can be prepared by the procedure described in Examples 3 and 5 of U.S. Pat. No. 4,275,073.

The procedure of Examples 1–3 was followed using 7-methylpyrazolopentathiepin (0.86 g, 3.58 mmol) instead of 7-phenylpyrazolopentathiepin, acetone (40 mL). methylene chloride (10 mL), and 23% aqueous ammonium sulfide (2.6 mL, 8.8 mmol). An additional 1.3 mL of aqueous ammonium sulfide was added over 15 min followed by an additional 1 h reaction time. The crude product was flash chromatographed on silica gel (column size: 5.1×20.3 cm, 50% methylene chloride/-hexane eluent, 50 mL fractions) to give: 150 mL, nil; 100 mL, sulfur (unweighed); 1000 mL, nil; 400 mL, 20 mg recovered starting pentathiepin; 400 mL, 110 mg 3,3-dimethyl-7-methyl-1,2,4,5-pyrazolotetrathiepin as an off-white solid, nmr(90 MHz) δ 7.56(s, 1H), 3.88(s, 3H), 2.1(s, 3H), 1.7(s, 3H); mp 104°–105.5° (ether/hexane). Continued elution gave: 500 mL, 230 mg of a mixture of 2,2-dimethyl-7-methyl-1,3,4,5-pyrazolotetrathiepin, and the 3,3-dimethyl isomer; 400 ml, 80 mg of 2,2-dimethyl-7-methyl-1,3,4,5-pyrazolotetrathiepin, nmr(80 MHz)δ 7.5(s, 1H), 3.9(s, 3H), 1.72(s, 6H).

The reaction was repeated on a 5× scale. The products were further purified by HPLC (silica gel, methylene chloride eluent) to give: 600 mg 3,3-dimethyl-7-methyl-1,2,4,5-pyrazolotetrathiepin; (Example 4) mp 106°–108° (ether/hexane); ir(KBr) 3090, 1500, 1355, 1346, 1160, 1141, 1104, 725, 690, 620.

Anal. calcd for C$_7$H$_{10}$N$_2$S$_4$: C, 33.58; H, 4.03; Found: C, 33.70; H, 4.07.

and 400 mg 2,2-dimethyl-7-methyl-1,3,4,5-pyrazolotetrathiepin; (Example 5) mp 110°–112.5° (ether/hexane); ir(KBr) 1500, 1360, 1345, 1145, 1102, 725, 691, 645, 622.

Anal. calcd for C$_7$H$_{10}$N$_2$S$_4$: C,33.58; H, 4.03; Found: C, 33.39; H, 4.09.

The reaction was repeated on a 10X scale. Further purification of the product by HPLC (silica gel, methylene chloride eluent) gave in addition to 2,2-and 3,3-dimethyl-7-methylpyrazolotetrathiepins, 4,4-dimethyl-7-methyl-1,2,3,5-pyrazolotetrathiepin as a crystalline solid: m.p. 128°–135°.

To further prove the identity of the products, an x-ray structure analysis of 2,2-dimethyl-7-methyl-1,3,4,5-pyrazolotetrathiepin confirmed its structure.

The compounds of Examples 1–5 and other compounds which can be prepared using this procedure are listed in Table 1.

TABLE 1

| Ex. No. | R | R$^1$ | X | Y | Z | m.p. (°C.) |
|---|---|---|---|---|---|---|
| 1 | —phenyl | H | S and C(CH$_3$)$_2$ | S | S and C(CH$_3$)$_2$ | |
| 2 | —phenyl | H | C(CH$_3$)$_2$ | S | S | 140.5–143.5 |
| 3 | —phenyl | H | S | S | C(CH$_3$)$_2$ | 134.5–135.5 |
| 4 | —CH$_3$ | H | S | C(CH$_3$)$_2$ | S | 106–108 |
| 5 | —CH$_3$ | H | C(CH$_3$)$_2$ | S | S | 110–112.5 |
| 6 | —C$_2$H$_5$ | H | S | C(CH$_3$)$_2$ | S | |
| 7 | —CH(CH$_3$)$_2$ | H | S | S | C(CH$_3$)$_2$ | |
| 8 | —(CH$_2$)$_4$CH$_3$ | H | S | S | C(CH$_3$)$_2$ | |
| 9 | —CH$_2$CH(CH$_3$)$_2$ | H | C(CH$_3$)$_2$ | S | S | |
| 10 | —C(CH$_3$)$_3$ | H | C(CH$_3$)$_2$ | S | S | |

TABLE 1-continued

R¹ at top of pyrazole; R-N on pyrazole; ring fused with S—X, Y, S—Z

| Ex. No. | R | R¹ | X | Y | Z |
|---|---|---|---|---|---|
| 11 | cyclopentyl-S- | H | S | S | C(CH₃)₂ |
| 12 | cyclohexyl-S- | H | C(CH₃)₂ | S | S |
| 13 | -CH₂-phenyl | H | C(CH₃)₂ | S | S |
| 14 | phenyl | Cl | C(CH₃)₂ | S | S |
| 15 | phenyl | CH₃ | S | S | C(CH₃)₂ |
| 16 | 4-Br-phenyl | H | S | S | C(CH₃)₂ |
| 17 | 4-NO₂-phenyl | H | C(CH₃)₂ | S | S |
| 18 | 4-OCH₃-phenyl | H | C(CH₃)₂ | S | S |
| 19 | 3,5-diBr-phenyl | H | S | S | C(CH₃)₂ |
| 20 | 3-F-4-Cl-phenyl | H | S | S | C(CH₃)₂ |
| 21 | 4-F-phenyl | H | S | S | C(CH₃)₂ |
| 22 | —CH₃ | H | C(CH₂CH₃)₂ | S | S |

TABLE 1-continued

[Structure with R-N, R¹, S-X, Y, S-Z on pyrazole-tetrathiepin framework]

| Ex. No. | R | R¹ | X | Y | Z | m.p. (°C.) |
|---|---|---|---|---|---|---|
| 23 | phenyl | H | S | S | C(CH₂CH₃)₂ | |
| 24 | phenyl | H | cyclohexyl-S | S | S | |
| 25 | phenyl | H | S | S | cyclohexyl | |

EXAMPLE 26

2,2-Dimethyl-6-methyl-1,3,4,5-pyrazolotetrathiepin

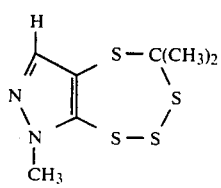

(A) 6-Methylpyrazolopentathiepin was prepared by the following procedure.

CAUTION:Dimethylformamide is embryotoxic.

A solution of 1-methylpyrazole (8.2 g, 0.10 mol) in 250 mL of dry ether was chilled to −20° and stirred while 1.6 M n-butyl lithium in hexane (63 mL, 0.10 mol) was added dropwise over 30 min. The resulting slurry was stirred at −20° for another 30 min, powdered sulfur (3.2 g, 0.10 g-atom) was added, and the cooling bath was removed. After adding 50 mL of dry 1,2-dimethoxyethane to aid stirring, the mixture was stirred at room temperature for 1 h, then chilled in ice while adding sulfur monochloride (2.4 mL, 40.5 g, 0.30 mol) dropwise over 20 min. Much gummy solid remained on the walls of the flask. Dimethylformamide (25 mL) was added and stirring was continued overnight at room temperature. The mixture was evaporated to dryness, and the residue was dissolved in dichloromethane.

The solution was washed with water and brine, dried over magnesium sulfate, and evaporated to leave 18.4 g of semisolid. Chromatography over 400 g of silica gel (dichloromethane/petroleum ether gradient) gave 3.0 g (12%) of crude 6-methylpyrazolopentathiepin as an off-white solid, mp 57°-60°; ir(nujol) 1150, 980, 885, 735 cm⁻¹; nmr (CDCl₃) 3.92 (3,s), 7.52 (1,s); nmr (CD₃SOCD₃) 3.90 (3,s), 7.73 (1,s); mass spectrum 239.8952 (C₄H₄N₂S₅=239.8972), 175.9517 (C₄H₄N₂S₃=175.9536).

Anal. calcd for C₄H₄N₂S₅: C, 19.99; H, 1.68; N, 11.65 S, 66.68; Found: C, 20.01 H, 1.77 N, 11.77 S, 68.01 19.95; 1.74; 11.72; 67.05.

Crystallization of the crude product from etherpetroleum ether gave pale yellow crystalline 6-methylpyrazolopentathiepin, mp 61°-95°. After standing at room temperature for 3 days, the same sample melted sharply at 89°-92°. Ir, nmr, tlc, and mass spectrum were the same as the low melting crystalline modification isolated above by chromatography.

Anal. calcd for C₄H₄N₂S₅: C, 19.99; H, 1.68; N, 11.65; S, 66.68; Found: C, 19.98 H, 1.84 N, 11.61 S, 67.60 19.94; 1.82; 11.49; 69.13 68.76.

(B) When the procedure of Examples 1–3 is followed using 6-methylpyrazolopentathiepin instead of 7-phenylpyrazolopentathiepin, the desired product, 2,2-dimethyl-6-methyl-1,3,4,5-pyrazolotetrathiepin, would be obtained as well as the isomeric products, 3,3-dimethyl-6-methyl-1,2,4,5-pyrazolotetrathiepin and 4,4-dimethyl-6-methyl-1,2,3,5-pyrazolotetrathiepin.

The compound of Example 26 and other compounds which could be prepared using this procedure are listed in Table 2.

TABLE 2

[Structure with R¹, N-N-R, S-X, Y, S-Z on pyrazole ring]

| EX. NO. | R | R¹ | X | Y | Z | m.p. (°C.) |
|---|---|---|---|---|---|---|
| 26 | —CH₃ | H | C(CH₃)₂ | S | S | |
| 27 | —CH₃ | H | S | S | C(CH₃)₂ | |
| 28 | phenyl | H | S | S | C(CH₃)₂ | |
| 29 | phenyl | H | C(CH₃)₂ | S | S | |
| 30 | —CH₂CH₃ | H | S | S | C(CH₃)₂ | |
| 31 | —CH₂CH₃ | H | C(CH₃)₂ | S | S | |
| 32 | —CH(CH₃)₂ | H | S | S | C(CH₃)₂ | |
| 33 | —(CH₂)₄CH₃ | H | S | S | C(CH₃)₂ | |

TABLE 2-continued

| EX. NO. | R | R¹ | X | Y | Z | m.p. (°C.) |
|---|---|---|---|---|---|---|
| 34 | —CH₂CH(CH₃)₂ | H | C(CH₃)₂ | S | S | |
| 35 | —C(CH₃)₃ | H | C(CH₃)₂ | S | S | |
| 36 |  | H | S | S | C(CH₃)₂ | |
| 37 |  | H | C(CH₃)₂ | S | S | |
| 38 | —CH₂— | H | C(CH₃)₂ | S | S | |
| 39 |  | Cl | C(CH₃)₂ | S | S | |
| 40 |  | CH₃ | S | S | C(CH₃)₂ | |
| 41 |  | H | S | S | C(CH₃)₂ | |
| 42 |  | H | C(CH₃)₂ | S | S | |
| 43 |  | H | C(CH₃)₂ | S | S | |
| 44 |  | H | S | S | C(CH₃)₂ | |
| 45 |  | H | S | S | C(CH₃)₂ | |
| 46 |  | H | S | S | C(CH₃)₂ | |
| 47 | —CH₃ | H | C(CH₂CH₃)₂ | S | S | |
| 48 |  | H | S | S | C(CH₂CH₃)₂ | |
| 49 |  | H |  | S | S | |
| 50 |  | H | S | S |  | |

DOSAGE FORMS

The antimycotic agents of this invention can be administered by any means that effects contact of the active ingredient with the agent's site of action in the body. The normal dosage form of these agents is topical application.

The dosage form may be a solution, gel, emulsion, suspension, paste, ointment, powder, or other suitable formulation. The dosage of the drug administered will, of course, vary depending upon known factors such as the pharmacodynamic characteristics of the particular agent, age, health, and weight of the recipient, the frequency of treatment, and the effect desired. Generally in man, a daily topical dosage of active ingredient will be from about 5 milligrams to about 50 milligrams per application, although lower and higher amounts can be used. The active ingredient, the drug, can be employed in useful compositions according to the present invention in such dosage forms as solution, semisolid, and solid form. These dosage forms preferably deliver from about 5 milligrams to about 50 milligrams of active ingredient per application, with a range from about 10 milligrams to about 25 milligrams per application being preferred. In these dosage forms the antimycotic composition will contain at least one non-toxic pharmaceutically acceptable carrier for the active ingredient.

Examples of the non-toxic carriers or adjuvants are viscosity enhancers such as bentonite, celluloses (e.g. methylcellulose, ethylcellulose, and carboxy methylcellulose), polyvinylpyrrolidone (PVP) tragacanth, glyceryl monostearate, cetyl alcohol, stearyl alcohol, synthetic spermaceti, and stearic acid; pH modifiers such as dibasic sodium phosphate, citric acid, and sodium hydroxide; preservatives such as methylparaben, propylparaben, benzoic acid, and benzyl alcohol; stability enhancers such as sodium bisulfite and ascorbic acid; coloring such as food, drug and cosmetic (FD&C) and drug and cosmetic (D&C) colors certified by the Food and Drug Administration (FDA); solvents such as water, alcohol (e.g. ethyl alcohol and isopropyl alcohol), polyethylene glycol, and propylene glycols; suspending agents such as kaolin, celluloses (e.g. methylcellulose, ethylcellulose, and carboxy methylcellulose), acacia and tragacanth; emulsifying agents such as glyceryl stearate, decyloleate, cetearyl alcohol, polysorbate 60, polysorbate 80, and triethanolamine; and humectants such as myristyl myristate.

A typical embodiment of the pharmaceutical composition of this invention is as follows: (all percentages are by weight of composition)

| Cream | |
|---|---|
| Pyrazolotetrathiepin | 0.5–10% |
| Polyethylene glycol 400 | 1–20% |
| Propylene glycol | 1–10% |
| Carboxypolymethylene | 1–10% |
| Monoamylamine | 1–10% |
| Titanium dioxide | 0.1–2% |
| Butylated hydroxytoluene | 0.1% |
| Stearic acid | 2–10% |
| Water | 1–90% |
| Solution | |
| Pyrazolotetrathiepin | 0.5–10% |
| Polyethylene glycol 400 | 1–99% |
| Butylated hydroxytoluene | 0.1% |

UTILITY

The fused pyrazolotetrathiepins of the invention are useful as antimycotic agents. The basis for this utility is that the compounds exhibit in vitro antifungal activity as shown in Table 3. The data is a result of different state of the art protocols, which employ either agar dilution or microtiter broth dilution techniques.

The test organisms used are two yeasts, *Candida albicans* ATCC 11651 (CAND-1), *C. albicans* ATCC e10231 (CAND-2) and two dermatophyte strains. *Microsporum gypseum* ATCC e9083 (MICRO-1) and *Trichophyton rubrum* ATCC 18756 (TRICH-1). These organisms are standardized to a concentration of $10^7$ organisms/mL, aliquoted and frozen at $-70°$.

The compounds are dissolved in dimethyl sulfoxide (DMSO) and tested at specific concentrations required for the particular assay.

Appropriate standards are included with each assay. Their minimal inhibitory concentrations (MIC) values are shown in Table 4 according to the particular protocol used. Stock solutions of standard agents are stored at $-70°$ and diluted the day of the assay.

Protocols 1 & 2 use a modification of the agar dilution method (Barry, A. L., The Antimicrobic Susceptibility Test: Principles and Practices, Lea and Febiger, 1976) with either Sabouraud dextrose agar (protocol 1) or Eagle's Minimum Essential Medium Agar (EMEM) (protocol 2).

The compound is tested at four specific concentrations within the range of 100 µg/mL–0.04 µg/mL and is incorporated directly into 20 mL molten agar (50°). The plates are then inoculated with the spore suspensions of MICRO-1 and TRICH-1 at $5 \times 10^6$ spores/mL using a multi point inoculator. The plates are incubated at ambient temperature for seven days and the MIC values determined.

Protocol 3 is a microtiter broth dilution assay that has been adapted for dermatophytes using EMEM and is described by Granade and Artis, *J. Clin. Micro.*, 6, 1043–1047 (1982). Both strains of dermatophytes, MICRO-1 and TRICH-1 are diluted in broth to achieve an inoculum of $1 \times 10^4$ spores/mL. The compound is serially diluted from 100 µg/mL to 0.4 µg/mL in 10-two fold dilutions. The test is incubated at 30° for 72 hrs and the MIC values are determined. The minimum fungicidal concentration (MFC) assay is performed using the 72 hr microtiter plates. (Szoka, F., *Mycology Observer*, November–December, 1983). These plates are shaken vigorously and 1µl/broth well is transferred with a micropipetter onto the appropirate well on a 24 well agar (EMEM) plate. These plates are then incubated at 30° for 72 hrs and read for MFC's.

Protocols 4 and 5 both utilize a standard microtiter broth dilution method described by Barry (Antimicrobic Susceptibilty Test: Principles and Practices, Lea and Febiger, 1976) but each uses a different medium. Protocol 4 uses Yeast Nitrogen Base broth pH 7.0 [Shadomy, S. *Applied Microbiology*, 17, 871–877 (1969)] while protocol 5 uses EMEM broth pH 7.4. The test organisms, CAND-1 and CAND-2 are diluted in the appropriate broth to achieve an inoculum of $1 \times 10^4$ CFUs/mL.

The compounds are tested from 100 µg/mL–0.4 µg/mL in 10-two fold serial dilutions and the assay is incubated at 37°, 5% $CO_2$ for 24 hrs. MFC's are then determined as previously described but the plates are incubated under the conditions appropriate for Candida spp.

TABLE 3

IN VITRO DILUTION MINIMAL INHIBITORY CONCENTRATIONS MIC [MFC] µg/mL

| EX. NO. | CAND-1 | CAND-2 | PROTOCOL | MICRO-1 | TRICH-1 | PROTOCOL |
|---|---|---|---|---|---|---|
| 1 | >100 | >100 | 4 | 4.0 | ≦0.8 | 1 |
| 2 | Inactive at 100 µg/mL | | | 1.0 | 0.2 | 2 |
| 3 | Inactive at 100 µg/mL | | | 1.0 | 1.0 | 2 |
| 4 | 25[50] | 25[50] | 5 | 12.5[25] | 12.5[25] | 3 |
| 5 | 12.5 | 6.3 | 4 | 4.0 | 4.0 | 1 |
|   | 3.2 | 1.6 | 5 | | | |

TABLE 4

MIC VALUES (µg/mL)* OF THE STANDARDS

| Protocol/Standards | Test Organisms | | | |
|---|---|---|---|---|
|  | CAND-1 | CAND-2 | MICRO-1 | TRICH-1 |
| Protocol 1 Griseofulvin | N.T. | N.T. | 2.0 ± 0.7 | 1.8 ± 0.7 |
| Protocol 2 Griseofulvin | N.T. | N.T. | 4.5 ± 3.0 | 9.4 ± 4.0 |
| Protocol 3 Griseofulvin | N.T. | N.T. | 5.4 ± 2.0 | 6.3 ± 0.0 |
| Protocol 4 | | | | |
| Amphotericin B | 0.6 ± 0.2 | 0.5 ± 0.3 | N.T. | N.T. |
| 5-Fluorocytosine | 0.7 ± 0.2 | 1.1 ± 0.4 | N.T. | N.T. |
| Ketoconazole | 0.15 ± 0.1 | 0.22 ± 0.04 | N.T. | N.T. |
| Miconazole | 0.36 ± 0.12 | 0.5 ± 0.2 | N.T. | N.T. |
| Nystatin | 6.0 ± 2.0 | 5.0 ± 1.5 | N.T. | N.T. |
| Protocol 5 | | | | |
| Amphotericin B | 0.5 ± 0.3 | 0.7 ± 0.3 | N.T. | N.T. |
| 5-Fluorocytosine | 1.1 ± 0.4 | 1.3 ± 0.4 | N.T. | N.T. |
| Ketoconazole | 0.3 ± 0.04 | 0.2 ± 0.04 | N.T. | N.T. |
| Miconazole | 0.5 ± 0.4 | 0.5 ± 0.4 | N.T. | N.T. |
| Nystatin | 5.0 ± 0 | 4.5 ± 1.0 | N.T. | N.T. |

*MIC values are the mean of five determinations ± standard deviation.
N.T.: Not tested

What is claimed is:
1. A compound having the formula:

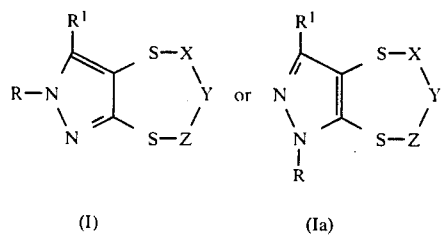

(I)        (Ia)

wherein
R is alkyl of 1–6 carbon atoms, cycloalkyl of 5–6 carbon atoms, benzyl, or phenyl which may be substituted with up to two groups selected from F, Cl, Br, $NO_2$, or $OCH_3$;
$R^1$ is hydrogen, halogen, or alkyl of 1–6 carbon atoms; and
X, Y, and Z are independently selected from S and $CR^2R^3$ where $R^2$ and $R^3$ individually are alkyl of 1–4 carbon atoms or together are alkylene of 3–6 carbon atoms,
provided that:
(1) one of X, Y, and Z must be $CR^2R^3$ and two of X, Y, and Z are S; and
(2) when R is phenyl; Y must be S.
2. The compound of claim 1 wherein R is phenyl or methyl.
3. The compound of claim 1 wherein $R^1$ is H.

4. The compound of claim 1 wherein R is phenyl or methyl; $R^1$ is H; and Y is S.

5. The compound of claim 4 wherein $R^2$ and $R^3$ individually are methyl or taken together are pentamethylene.

6. The compound of claim 1 which is 2,2-dimethyl-7-methyl-1,3,4,5-pyrazolotetrathiepin.

7. The compound of claim 1 which is 2,2-dimethyl-7-phenyl-1,3,4,5-pyrazolotetrathiepin.

8. The compound of claim 1 which is 4,4-dimethyl-7-methyl-1,2,3,5-pyrazolotetrathiepin.

9. The compound of claim 1 which is 4,4-dimethyl-7-phenyl-1,2,3,5-pyrazolotetrathiepin.

10. The compound of claim 1 which is 3,3-dimethyl-7-methyl-1,2,4,5-pyrazolotetrathiepin.

11. An antimycotic pharmaceutical composition comprising a suitable pharmaceutical carrier and an antimycotic effective amount of at least one compound of claim 1.

12. An antimycotic pharmaceutical composition comprising a suitable pharmaceutical carrier and an antimycotic effective amount of at least one compound of claim 2.

13. An antimycotic pharmaceutical composition comprising a suitable pharmaceutical carrier and an antimycotic effective amount of at least one compound of claim 3.

14. An antimycotic pharmaceutical composition comprising a suitable pharmaceutical carrier and an antimycotic effective amount of at least one compound of claim 4.

15. An antimycotic pharmaceutical composition comprising a suitable pharmaceutical carrier and an antimycotic effective amount of at least one compound of claim 5.

16. An antimycotic pharmaceutical composition comprising a suitable pharmaceutical carrier and an antimycotic effective amount of at least one compound of claim 6.

17. An antimycotic pharmaceutical composition comprising a suitable pharmaceutical carrier and an antimycotic effective amount of the compound of claim 7.

18. An antimycotic pharmaceutical composition comprising a suitable pharmaceutical carrier and an antimycotic effective amount of the compound of claim 8.

19. An antimycotic pharmaceutical composition comprising a suitable pharmaceutical carrier and an antimycotic effective amount of the compound of claim 9.

20. An antimycotic pharmaceutical composition comprising a suitable pharmaceutical carrier and an antimycotic effective amount of the compound of claim 10.

21. A method for the treatment of fungal infections in a mammal comprising administering to the mammal an antimycotic amount of a compound of claim 1.

22. A method for the treatment of fungal infections in a mammal comprising administering to the mammal an antimycotic amount of a compound of claim 2.

23. A method for the treatment of fungal infections in a mammal comprising administering to the mammal an antimycotic amount of a compound of claim 3.

24. A method for the treatment of fungal infections in a mammal comprising administering to the mammal an antimycotic amount of a compound of claim 4.

25. A method for the treatment of fungal infections in a mammal comprising administering to the mammal an antimycotic amount of a compound of claim 5.

26. A method for the treatment of fungal infections in a mammal comprising administering to the mammal an antimycotic amount of a compound of claim 6.

27. A method for the treatment of fungal infections in a mammal comprising administering to the mammal an antimycotic amount of the compound of claim 7.

28. A method for the treatment of fungal infections in a mammal comprising administering to the mammal an antimycotic amount of the compound of claim 8.

29. A method for the treatment of fungal infections in a mammal comprising administering to the mammal an antimycotic amount of the compound of claim 9.

30. A method for the treatment of fungal infections in a mammal comprising administering to the mammal an antimycotic amount of the compound of claim 10.

* * * * *